United States Patent [19]

Kim et al.

[11] 4,294,616
[45] Oct. 13, 1981

[54] ELECTRICAL CONTACTS

[75] Inventors: Han J. Kim, Greensburg, Pa.; Thomas E. Peters, Chelmsford; John Gustafson, Harvard, both of Mass.

[73] Assignee: GTE Products Corporation, Stamford, Conn.

[21] Appl. No.: 628

[22] Filed: Jan. 2, 1979

[51] Int. Cl.³ .............................................. H01H 1/02
[52] U.S. Cl. ........................................ 75/234; 75/206; 200/266; 428/565; 428/929
[58] Field of Search ............... 75/206, 234; 428/929; 428/565; 200/266

[56] References Cited

U.S. PATENT DOCUMENTS

| | | | |
|---|---|---|---|
| 3,954,459 | 5/1976 | Schreiner et al. | 75/206 |
| 4,011,052 | 3/1977 | Davies | 200/266 X |
| 4,115,325 | 9/1978 | Santala et al. | 75/234 |
| 4,138,251 | 2/1979 | Hirsbrunner et al. | 75/234 |
| 4,141,727 | 2/1979 | Shida et al. | 75/234 X |
| 4,204,863 | 5/1980 | Schreiner | 75/234 |

FOREIGN PATENT DOCUMENTS 5421284  7/1979  Japan ..................................... 75/206

*Primary Examiner*—Richard E. Schafer
*Attorney, Agent, or Firm*—Robert E. Walter

[57] ABSTRACT

An electrical contact of the type having a working surface and comprising a ductile metal and weld inhibiting material includes a wetting agent present in an amount sufficient to reduce the surface energy between said contact surface and the liquid phase of the ductile metal. Improved wettability of the surface results in reduced arc erosion due to the spattering loss of ductile metal. Also, described is a method for selecting and testing proposed additives.

5 Claims, 1 Drawing Figure

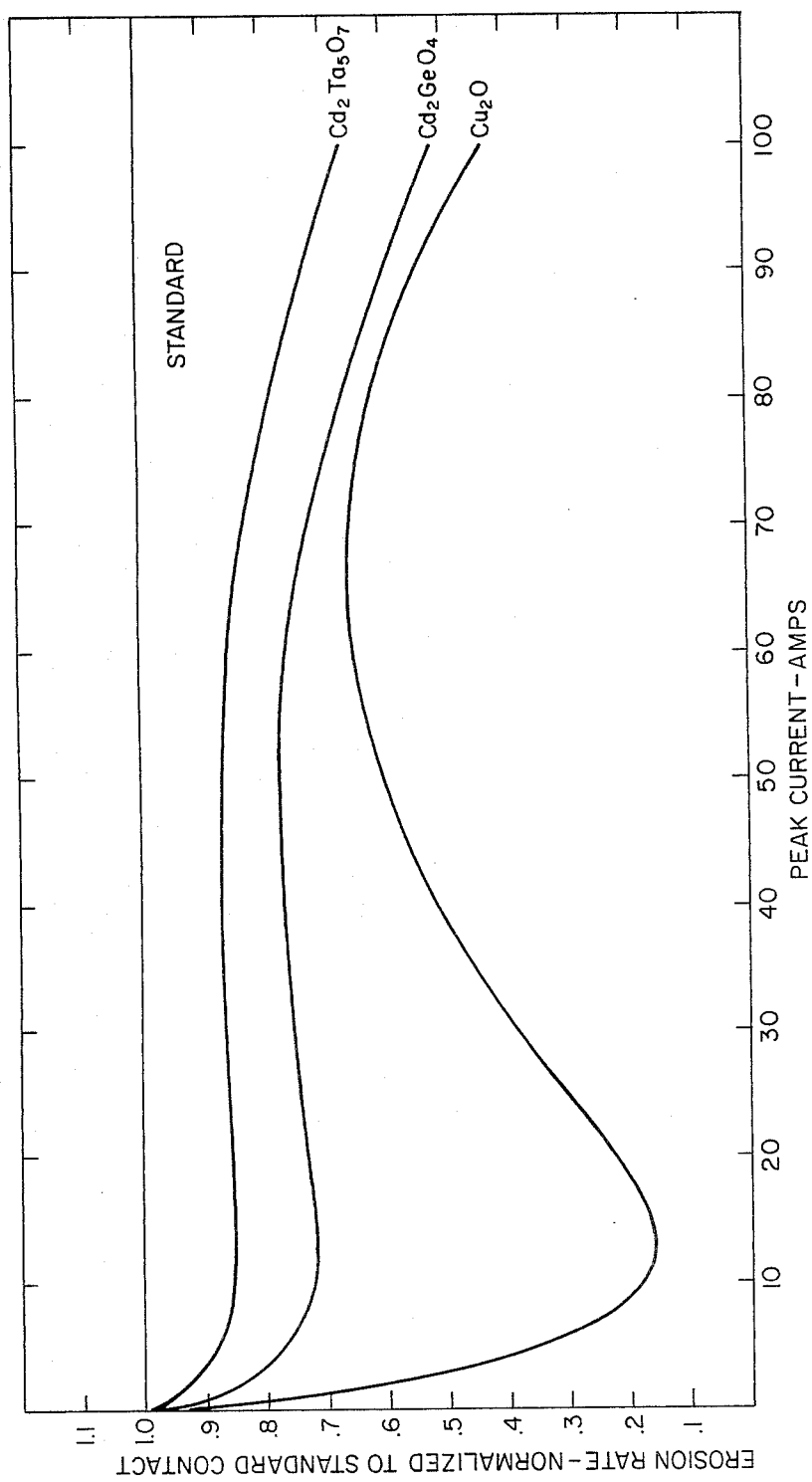

ELECTRICAL CONTACTS

This invention relates to electrical contacts which are typically used on contact pieces in medium to high voltage switching apparatus, more particularly to contact materials of the silver-cadmium oxide type.

To be suitable for the above applications, the contact material should have high thermal conductivity, high electrical conductivity, high resistance to corrosion, high mechanical strength, low contact resistance, good arc-interrupting cababilities, good formability and fabricability, and minimal tendency for interfacial welding or sticking and maximum resistance to arc erosion.

It is known to make electrical contacts from a conductive material and an additive material that tend to inhibit welding by weld embrittlement. The conductive material imparts high electrical and thermal conductivity to the contact while the additive, which is usually in the form of a metal oxide, contributes to the desirable properties of weld resistance, arc extinguishing, arc erosion resistance and increased strength properties of the overall contact material.

In practice, silver is preferable for the conductive material and cadmium oxide is preferable as a weld inhibiting material. However, there is substantiation, theoretical and empirical, that other conductive material could be used, particularly copper and possibly other highly conductive materials such as gold and platinum. The oxides of zinc, tin, indium, antimony, bismuth and lead may be used to impart the weld inhibiting characteristics to the conductive material.

It is known in the prior art to improve the desired properties of the electrical contact material by a third material added to the mixture of conductive material and embrittling material. The following discussion is relevant to additives of a third material.

U.S. Pat. No. 3,969,112 to Kim and Reid describes the addition of an alkali metal to a mixture of silver and cadmium oxide prior to the sintering step to improve the assintered densities of the resultant alloy material.

U.S. Pat. No. 3,694,197 to Zdanuk et al. discloses that reduced arc erosion is obtained in silver-cadmium oxide alloys by adding beryllium, cerium, scandium, antimony, gallium, indium, strontium, yttrium and thallium metals.

U.S. Pat. No. 3,893,821 to Davies discloses the addition of lanthanum strontium chromite to a silver cadmium oxide contact material.

U.S. Pat. No. 4,011,053 to Davies discloses the addition of an oxide of a metal selected from Group IA and IIA of the periodic table to an electrical contact material.

U.S. Pat. No. 3,785,810 to Durrwachter et al. discloses a silver cadmium oxide contact material having at least two additive other alloy components selected from the group consisting of calcium, antimony, magnesium, beryllium, aluminum, tin, manganese and zirconium.

In two separate articles, Proceedings of the 17th Holm Conference on Electrical Contacts, pp. 16–25, 1971 and Proceedings of the 18th Holm Conference on Electrical Contacts, pp. 333–348, 1972, Shen, Zdanuk and Krock studied the effects of numerous single element additions on the physical and electrical properties of silver cadmium oxide contact materials.

Heretofore, to obtain improved weld inhibiting properties, the amount of weld inhibiting material has been increased with the attendant result that the bulk properties, i.e. electrical conductivity, of the final material are unfavorably effected. Prior art studies relating to an additive of another material to the metal and weld inhibiting material have attributed observed differences to microstructual changes induced by the third material or to low work function and arc dispersive effects of the third material itself. As distinguished from the works of prior researchers, the present invention describes a method of selecting a third material which operates to control a specific mechanism causing erosion of the contact.

SUMMARY OF THE INVENTION

Electrical contact materials comprising a ductile metal and a weld inhibiting material are increasingly being used as contact materials for a variety of switching applications. Silver-cadmium oxide is extensively used because of its excellent arc erosion resistance and antiwelding properties. Although silver-cadmium oxide erodes at a slower rate than most other contact materials, there is, nevertheless, a loss of material during arcing cycles. Generally, two modes of material loss can be characterized: (1) the vaporization and/or decomposition of the contact material, and (2) the blow-off or spattering loss of droplets of the ductile metal used in the contact material. The present invention is particularly directed to the suppresion of the blow-off or spattering mode of material loss.

In accordance with the principles of the present invention, there is provided an electrical contact material comprising a ductile metal or metal alloy having a relatively high electrical and thermal conductivity, a sufficient amount of material to impart weld inhibiting qualities to said contact, and a wetting agent present in an amount sufficient for reducing surface energy between said contact surface and the liquid phase of said metal or alloy.

DRAWINGS

FIG. 1 illustrates a comparision of erosion rates in graph form.

DETAILED DESCRIPTION

The electrical contact material comprises a ductile metal or metal alloy having relatively high electrical and thermal conductivity for imparting these desirable characteristics to the contact. Silver is ideally suited for use as the conductive metal due to its chemical nonreactivity and commercial availability. It is contemplated that other metals such as copper, gold or platinum together with alloys thereof may also be used.

A sufficient amount of a weld inhibiting material is included with the ductile metal alloy to impart embrittlement qualities to the final electrical contact. The weld embrittlement material which preferably does not alloy with the ductile metal contributes to the breaking of the welds which form when contact is established between electrical contacts. This property can be measured according to a standard ASTM weld test wherein the weld strength of contacts which are closed and subjected to a specific current at a specific voltage are separated and the force due to welding of the contacts is measured. Typical weld inhibiting materials include oxides, especially the oxides of antimony, indium, tin, zinc, bismuth and cadmium.

Since the weld inhibiting material is generally a poor electrical and thermal conductor and has poor mechanical properties, it is generally preferable that the electrical contact material comprise a major portion by weight ductile metal and a minor portion by weight of the embrittlement material. The addition of an excess amount of weld inhibiting material undesirably reduces the conductivity of the electrical contact. Preferably the electrical conductivity of the final contact is greater than about 40 percent I.A.C.S. and even more preferably greater than about 50 percent I.A.C.S. The aforementioned value of electrical conductivity is in reference to those standards known in the art as the International Annealed Copper Standards (I.A.C.S.) wherein pure copper is rated as possessing 100 percent conductivity. More specifically pure copper in accordance with the above standards is rated at 10.371 ohms circular mils/ft.

To obtain the desirable weld embrittlement properties of the contact, the embrittlement material should be at least uniformly distributed on the surface of the contact in the metal matrix. According to one method of preparing contacts, the ductile metal and metal oxide embrittlement material are intimately mixed by blending the powders of the materials. The powder mixture is pressed into a compact and the compact is sintered by heating and pressing.

In accordance with another process for preparing contact materials, the ductile metal is alloyed with another metal or second metal which can be oxidized at a subsequent time to form the embrittlement material. It is required that the second metal be oxidized more readily than the first metal so internal oxidation results in a structure having the weld inhibiting characteristics of the contact. In practice, the preferred metals are silver for the first metal and cadmium for the second metal. Preferably the second metal is present in an amount up to its limit of solubility in the first metal or ductile metal. Typical other metals that may be used are copper for the first metal and zinc or tin for the second metal. According to the process, a powder mixture of the first metal and oxide of the second metal is heated, preferably in a reducing atmosphere at a temperature to avoid excessive sintering to form an alloy powder. The alloy powder is then heated in a suitable oxidizing atmosphere to internally oxidize the second metal. Electrical contacts prepared from powders made according to the above process have a uniform distribution of the oxide of the second metal in a matrix of the first metal. Due to the fact that the materials are substantially preoxidized, the compositions remain relatively stable during the conditions of operation.

According to another method of making electrical contacts, the alloy of the first metal and second metal may be formed directly into the proper contact shape which may be in the form of a thin strip or wire. Subsequent oxidation of the material at suitable conditions to oxidize the second metal and not the first metal results in a metal oxide of the second metal being formed within a matrix of the first metal. The oxide of the second metal is decreasingly present as the surface of the contact is penetrated.

In accordance with the principles of the present invention, the electrical contact includes a wetting agent present as an additive in the contact material in an amount sufficient for reducing the surface energy between the working surface of the contact and the liquid phase of the ductile metal or alloy. The wetting agent minimizes the spattering mode of erosion by lowering the surface energy of the contact thereby reducing the propensity of the ductile metal to form microscopic droplets on the contact surface. Preferably the wetting agent possesses the ability to substantially lower the surface tension of the liquid metal on the contact surface without otherwise significantly diminishing the physical, mechanical and electrical properties of the contact or its performance. Wetting agents that form alloys or intermetallic compounds with the ductile metal can reduce the electrical conductivity of the contact and should be avoided. Unless the wetting agent itself contributes to the final desired properties of the contact material, it is preferable to use only relatively small amounts of the wetting agent in proportion to the overall composition of the contact. Preferably small amounts of a wetting agent which imparts a high degree of wetting to the surface of the contact is homogeneously distributed over the working surface and dispersed in the metal matrix so that the entire working surface will have desirable wetting properties.

The wetting agent or material capable of forming a wetting agent should be selected to permit its incorporation into the contact under conditions of manufacture or use or permit the formation of the wetting agent during such conditions. More preferably the wetting agent is an oxide of a metal other than the ductile metal and has a substantially greater wettability with the liquid phase of the ductile metal than the wettability of the embrittlement material with the liquid phase of the ductile metal. By incorporating the wetting agent into the contact, the favorable properties of low surface energy are imparted to the contact to give increased surface wettability.

As hereinbefore mentioned, the in situ formation of the wetting agent is contemplated. When the wetting agent is a compound of the metal, the metal itself or other compound of the metal may be incorporated into the contact provided the wetting agent is subsequently formed. For example, when the wetting agent is a metal oxide, the metal in elemental form or other metal compound may be incorporated into the contact provided the metal oxide wetting agent is subsequently formed. It is contemplated that the metal or metal compound necessary for the formation of the wetting agent or the wetting agent itself may be present as a separate phase or alloyed with the ductile metal.

The wettability and relative surface energy of a wetting agent can be determined by measuring the contact angle between the liquid phase of the ductile metal and the wetting agent. A solid/liquid interface is present between the solid contact and liquid ductile metal. The contact angle which is equal to or greater than zero, is measured between the liquid and the solid wetting agent and is the angle at the line of contact between the solid and liquid as measured in the liquid phase. Although many methods may be used for measuring surface energy, it has been found that the following method is satisfactory for obtaining a relative comparison of the surface energies of candidate materials for wetting agents.

The contact angle between a molten metal and a metal oxide is measured by first pressing fine powder of the wetting agent into a compact. Next the compact is sintered by heating. The resulting product should have a flat surface free from surface contamination so that subsequent contact angle measurements are due to material differences alone rather than the nature of the surface. A short length of a small diameter wire of the ductile metal is placed on the surface of the compact.

The compact and ductile metal are heated to a temperature sufficient to liquify the metal and a photograph is taken. The contact angle is then approximated from the photograph. By comparing the contact angles of various proposed wetting agents with the contact angle formed between the ductile metal and weld inhibiting material, a wetting agent may be selected. The wetting agent should have a substantially smaller contact angle with the liquid phase of the ductile metal than the contact angle that the weld inhibiting material has with the liquid phase of the ductile metal.

In general, the electrical contact material comprises a major portion by weight ductile metal and a minor portion embrittlement material with the wetting agent comprising an amount replacing the embrittlement material and present in an amount from an effective amount which reduces the surface energy to an amount less than an amount which undesirably effects the desirable final properties of the electrical contact material. Typically, the contact comprises about 50 to about 95 percent by weight ductile metal, from about 5 to about 50 percent by weight weld inhibiting material and greater than about 0.001 percent by weight wetting agent.

The contact angle of silver with oxides was measured in accordance with the above procedure. The following oxides in the order set forth were found to exhibit increasing contact angles with the oxide of copper exhibiting the smallest contact angle and the oxide of aluminum exhibiting the largest contact angle. The oxides in order of decreasing wettability are copper oxide, germanium oxide, tantalum oxide, niobium oxide, yttrium oxide, cadmium oxide, cerium oxide, chromium oxide, cobalt oxide, iron oxide, ruthenium oxide, zirconium oxide, zinc oxide, and aluminum oxide.

To obtain an improved wetting angle in the final contact surface using a relatively small amount of wetting agent, it is desirable to employ a wetting agent having a substantially smaller contact angle with the liquid phase than the contact angle that the weld inhibiting material has with said liquid phase. Cadmium oxide has a contact angle of approximately 82°, yttrium oxide about 80° and niobium oxide about 73°. When added in relatively small amounts to the final contact material, niobium and yttrium oxides will not have a substantially smaller contact angle with the liquid silver phase so that a relatively small amount of these materials incorporated into the contact would not have a significant effect in reducing arc erosion. The oxides of copper, germanium and tantalum exhibited contact angles of 22°, 35° and 64° respectively. These materials have a contact angle substantially less than cadmium oxide and when properly incorporated into the final contact material in small amounts will result in a decrease in arc erosion due to spattering.

It was found that germanium and tantalum be present in the form of single oxide or double oxide compounds, are the most preferred materials for use with cadmium oxide. Their presence in small amounts did not seem to impart undesirable characteristics to the final contact. Although the silver cadmium oxide contact prepared with copper oxide displayed the most favorable wetting properties of those contacts tested, the contact exhibited undesirable cracking in the arc effected layer. Typical double oxides are formed as an oxide of the wetting agent and the weld inhibiting material. For germanium and tantalum the compounds have the chemical formula $Cd_2GeO_4$ and $Cd_2Ta_2O_7$.

With the silver-cadmium oxide contacts, the contact angle that the final electrical contact exhibits with the liquid ductile metal is substantially the same as the contact angle that cadmium oxide in substantially pure form exhibits with the liquid metal. With silver-cadmium oxide contacts containing a major portion of silver, it has been found that small amounts of well dispursed wetting agent can significantly reduce the droplet formation by reducing the surface energy between the ductile metal droplet and the final contact material. This results in reduced arc erosion by way of reduction of spattering.

Although the above work was done with silver-cadmium oxide materials, it is theorized that materials having a lower surface energy than the weld inhibiting material may be incorporated in electrical contact materials formed from other ductile materials and embrittlement material. The value of the material as a wetting agent can be measured by comparing its tendency to be wetted by the molten metal with the tendency of the weld inhibiting material to be wetted by the molten metal.

The following examples are given to enable those skilled in the art to more clearly understand and practice the present invention. They should not be considered as a limitation upon the scope of the invention, but merely as being illustrative and representative thereof.

Example 1—About 6 grams of cadmium oxide particles on the order of less than two microns is pressed using a pressure of 560 kg per $cm^2$ to obtain compacts 0.2 cm in thickness. The resulting compact is heated to a temperature of 915° C. at 15° C. per minute and held at the final temperature for about 1.5 hours to sinter the compact. After cooling, a short length of silver wire having a small diameter is placed on the surface of the compact. The compact and silver wire is heated to a temperature of about 1050° C. whereby the silver is in the liquid phase. A photograph is taken of the liquid silver on the surface of the contact at the above temperature. From the photograph the contact angle of the silver with the cadmium oxide compact is determined to be about 82°.

Example 2—In a manner similar to Example 1, the oxides of copper, germanium, tantalum, niobium and yttrium in powder form are pressed into a compact which is sintered. The contact angles are measured to give contact angles of 22, 35, 64, 73 and 80 degrees respectively.

Example 3—In a manner similar to Example 2, the contact angles of the oxides of cerium, cobalt, iron, ruthenium, zirconium, zinc and aluminum were measured. All of these oxides exhibited contact angles greater than the about 82° contact angle exhibited by cadmium oxide. The oxide of cerium exhibited contact angle of 94°.

Example 4—Submicron size silver powder is dry blended with cadmium oxide powder and a metal oxide wetting agent. The cadmium oxide and metal oxide wetting agent each have particle sizes of less than 2 microns as measured by a scanning electron microscope. The metal oxide is added in a quantity sufficient to occupy about one volume percent of the contact material. Lithium nitrate dissolved in distilled water is added to the powdered blend to form a slurry. The amount of lithium nitrate added is sufficient so as to result in a dry powder mixture having about 0.1 weight percent lithium nitrate. It is added for purposes of densification as set forth in U.S. Pat. No. 3,969,112. After drying and sieving, about 3 grams of the powdered blend containing the wetting agent and densification aid is pressed using a pressure of 560 kg per cm$^2$ to obtain compacts 0.2 cm in thickness having approximately 50 percent porosity. For comparison purposes, a compact not containing a wetting agent but including the densification aid is prepared. The compacts are heated for fired sintering to 915° C. at 15° C. per minute and held at that temperature for 1.5 hours for final sintering. Contacts are prepared according to the above procedure using the following blends of powder: (1) 21.3 grams of Ag, 3.55 grams of CdO and 0.15 grams of Cu$_2$O, (2) 21.3 grams of Ag, 3.54 grams of CdO and 0.16 grams of Cd$_2$GeO$_4$, (3) 21.3 grams of Ag, 3.45 grams of CdO and 0.25 grams of Cd$_2$Ta$_2$O$_7$, and (4) 21.3 grams of Ag, 3.70 grams of CdO.

Example 5—The procedure of Example 4 was repeated using powder blends containing germanium oxide and tantalum oxide represented by the formulae GeO$_2$ and Ta$_2$O$_5$.

Example 6—The erosion rates of the contacts prepared in Example 4 were measured in a static gap arc chamber. The electrode spacing was 0.5 mm. An arc was initiated by the application of a high voltage breakdown pulse of 15 kv and 2 microseconds duration which developed a conducting channel through which a capacitor bank was discharged. The parameters of the capacitor bank were chosen to give a half-sinusoid arc wave form of 8.3 millisecond duration and peak currents adjustable to 100 amps. The tests were carried out in an atmosphere of 80 percent nitrogen, 20 percent oxygen of 99.9 purity. The samples were subjected to $6 \times 10^3$ current pulses at a repition rate of one pulse every ten seconds. The low duty cycle eliminated any long term temperature rise in the contact assembly. The erosion of the contacts was determined by weighing the sample before and after arcing. The results of the test are illustrated in the drawing. The cathodic erosion rate for the materials containing the wetting agent, blends 1-3 of Example 4, are plotted in FIG. 1 relative to the erosion rate for the silver-cadmium oxide material without the wetting agent, blend 4 of Example 4. The error bars equal plus or minus one standard deviation and represent the amount of scatter of the measurements about the smoothing functions used to represent the data. The erosion rate for materials containing the additives is significantly less than that of the silver-cadmium oxide material without wetting agent, hereinafter called the standard contact. The difference is particularly pronounced at the higher currents where appreciable contact melting occurs and silver droplet loss is most pronounced. The ranking of the wetting agents obtained from the contact angle measurements is preserved in erosion rate measurements. That is copper oxide, the material with the lowest interfacial energy, (contact angle equal to 22°) is also the most effective of the wetting agents in lowering the erosion rate. Scanning electron microscope examination of the eroded cathodes reveal well formed droplets of silver, approximately one micron in diameter, on the surface of the standard contact. The well defined droplet is indicative of poor wettability between the droplet and the contact surface. The contact containing wetting agent have surfaces exhibiting a smooth morphology indicative of good wetting between the silver droplets and the cathode surface. The anode was the upper most electrode in the test. Material vaporized from the cathode condensed on the cooler anode causing an apparent weight increase at low current. This effect masked the true erosion rate of the material. Scanning electron microscope examination of the anode surfaces showed morphological differences similar to those noted for the cathodes. Well formed droplets of silver were on the surface of the standard contact while the surface containing the wetting agent additives were wetted by the the silver. Some cracking occurred in the anode surface employing copper oxide.

Example 7—The contacts prepared in accordance with the procedure set forth in Example 5 were tested and erosion rate lower than the standard contact material was noted. The absence of droplet formation on the contact surfaces indicates an improvement in the wetting behavior of the contacts containing wetting agent.

Example 8—Submicron size silver powder is dry blended with cadmium oxide powder having a particle size less than two microns. The resulting blend is about 85.2 percent silver by weight with the remainder cadmium oxide. Sufficient germanium dioxide is added in a quantity to occupy about one volume percent of the contact material. The germanium dioxide is added as an aqueous solution containing 3.85 grams per liter of germanium oxide per liter. The resulting slurry is mixed, dried and sieved. Next the powder is placed in an alumine boat and heated at about 10° C./min to a temperature of 350° C. in a nitrogen atmosphere containing about 10% hydrogen to effect reduction of the cadmium oxide and result in the formation of an alloy powder of cadmium and silver. The germanium oxide remains essentially unchanged. The resulting alloy powder is then oxidized at 350° C. to precipitate a dispersion of cadmium oxide within the grains of silver. After cooling to room temperature the powder is again sieved and is mixed with sufficient lithium nitrate in a methyl alcohol solution to result in a powder when dried having about 0.1 weight percent lithium nitrate. About 2 grams of the powder is pressed using a pressure of 2800 kg/cm$^2$ to obtain a compact about 0.25 cm in thickness having approximately 40 percent porosity. The compact is then sintered by heating according to the schedule set forth in Example 4. The above procedure is followed except for the germanium dioxide addition to produce an electrical contact not containing a wetting agent and hereinafter referred to as the standard contact.

Example 9—The contacts prepared as in Example 8 are tested according to the procedure set forth in Example 6. At an arc current of 200 amps., GeO was 84 percent of the erosion exhibited by the standard material.

The present invention has been described with reference to the specific embodiments thereof, it should be understood by those skilled in the art that various changes may be made and equivalence may be substituted without departing from the spirit and scope of the invention as set forth in the appended claims.

What is claimed is:

1. An electrical contact having a working surface consisting essentially of from about 50 to about 95 percent by weight silver or silver alloy, from about 5 to about 50 percent by weight of cadmium oxide, and an additional oxide selected from the oxides of germanium, tantalum, and mixtures thereof, said additional oxide being present in an effective amount sufficient to reduce the surface energy between said working surface and the liquid phase of said silver and being substantially homogeneously distributed on said surface in a silver matrix.

2. An electrical contact according to claim 1 wherein said wetting agent is a cadmium germanium oxide.

3. An electrical contact according to claim 1 wherein said wetting agent is a cadmium tantalum oxide.

4. An electrical contact according to claim 1 wherein said contact is sintered and said cadmium oxide and said additional oxide are substantially homogeniously distributed throughout said contact.

5. An electrical contact according to claim 1 wherein said cadmium oxide is formed by the internal oxidation of cadmium within a silver matrix.

* * * * *